(12) United States Patent
Masley et al.

(10) Patent No.: US 8,176,647 B2
(45) Date of Patent: May 15, 2012

(54) HAND SIZING TOOL

(75) Inventors: Francis J. Masley, Wilmington, DE (US); Stacey Lee, Southborough, MA (US); Ara Atkinson-Skinner, Bear, DE (US)

(73) Assignee: Masley Enterprises Inc., Wilmington, DE (US)

( * ) Notice: Subject to any disclaimer, the term of this patent is extended or adjusted under 35 U.S.C. 154(b) by 34 days.

(21) Appl. No.: 12/900,907

(22) Filed: Oct. 8, 2010

(65) Prior Publication Data

US 2012/0084990 A1 Apr. 12, 2012

(51) Int. Cl.
G01B 5/02 (2006.01)
A41H 1/02 (2006.01)
A61B 5/107 (2006.01)
(52) U.S. Cl. .......................................... 33/512; 33/2 R
(58) Field of Classification Search .................. 33/512, 33/2 R, 11, 17 R
See application file for complete search history.

(56) References Cited

U.S. PATENT DOCUMENTS

| | | | | |
|---|---|---|---|---|
| 1,997,920 | A * | 4/1935 | Bliss | 33/2 R |
| 2,531,477 | A * | 11/1950 | Smith | 33/3 A |
| 2,605,548 | A * | 8/1952 | Clarke | 33/2 R |
| 4,160,327 | A * | 7/1979 | Martin et al. | 33/512 |
| 4,173,074 | A * | 11/1979 | Newman et al. | 33/2 R |
| 4,360,972 | A * | 11/1982 | Montgomery | 33/17 R |
| 4,897,924 | A * | 2/1990 | Tepley | 33/2 R |
| 5,170,570 | A * | 12/1992 | Mays, Jr. | 33/512 |
| 5,285,785 | A * | 2/1994 | Meyer | 600/426 |
| 6,327,787 | B1 * | 12/2001 | Bonzagni et al. | 33/512 |
| 6,662,942 | B1 * | 12/2003 | Bonzagni | 206/278 |
| 2003/0056384 | A1 * | 3/2003 | Masley | 33/512 |

* cited by examiner

Primary Examiner — Christopher Fulton
(74) Attorney, Agent, or Firm — Connolly Bove Lodge & Hutz LLP

(57) ABSTRACT

A hand sizing tool includes a base platform and a secondary platform affixed to and raised above the base platform. The platforms include a palm heel indicia on the base platform and an index finger tip indicia on the secondary platform. Each of an index finger guide, an index finger measurement slider, and a palm width measurement slider extends out of the secondary platform, these elements being adapted for measuring the hand size.

11 Claims, 3 Drawing Sheets

HAND SIZING TOOL

BACKGROUND OF THE INVENTION

1. Field of the Invention

The field of the present invention is tools for measuring the size of hands for purposes of fitting gloves.

2. Background

The challenge for certain types of gloves, and thus for glove manufacturers, is to fit the wearer better while also providing sufficient tactility for the wearer. This challenge is especially acute for gloves intended for firefighting and military applications. In these applications, the wearer often requires significant hand protection, and such protection typically necessitates a relatively thick and non-stretchable glove. At the same time the wearer may need to perform tasks that require manipulation of relatively small objects such as the switches and buttons often found on radios, phones, and computers, or the wearer may need to operate a fire arm, an action for which a glove that properly fits to the trigger finger may be critical. The act of manipulating small objects with one's hands and the sense of touch is often referred to as tactility. For gloves, there is an inverse relationship between tactility and the thickness of the glove at the fingertip. Tactility is diminished as the distance increases between skin at the fingertip and the outer surface of the glove at the fingertip.

Therefore it is advantageous to the user to select and wear gloves that minimize the amount of excess material at the fingertips. This is especially the case with the index finger, because this finger is most often used in the manipulation of small objects. While wearers generally recognize the need for a close fit at the fingertip, especially for the index finger, too many glove sizing systems focus on measuring the length of the middle finger, which is generally the longest. In those sizing systems where the index finger is measured, the results are often not easily and accurately reproducible. Each of these problems leads to a fit for gloves that provides less tactility for the index finger than is desired by the wearer.

U.S. patent publication No. 2003/0056384, the disclosure of which is incorporated herein by reference in its entirety, discloses an example of a glove sizing system in which the index finger and the palm width of a hand are measured to determine the glove size for the hand. This system discloses using a printed hand sizing tool placed on a flat surface and positioning the hand to be measured using a pencil to perform the a measurement. As indicated above, because the hand is positioned using only a pencil, difficulties may be encountered in reproducing accurate measurements.

SUMMARY OF THE INVENTION

The present invention is directed toward a hand sizing tool having a base platform and a secondary platform affixed to and raised above the base platform. The platforms include a palm heel indicia on the base and an index finger tip indicia on the secondary platform. An index finger guide, an index finger measurement slider, and a palm width measurement slider each extend out of the secondary platform.

Several options may be incorporated into the hand sizing tool to provide additional functionality and/or better reproducibility of measurement results. As one option, the index finger guide is disposed between the index finger tip indicia and a partial middle finger indicia on the secondary platform. As another option, a leading edge of the index finger guide may extend out of the secondary platform at an angle of less than 90° toward the palm heel indicia. As another option, the height of the secondary platform may vary with respect to the base platform to accommodate a resting position of the hand. As yet another option, the distance by which the measurement end of the palm width measurement slider extends beyond the leading edge of the index finger guide, toward the palm heal indicia, may be varied to accommodate preferences in where the palm width measurement is taken on the hand. As yet another option, the distance by which the edge of the secondary platform extends beyond the leading edge of the index finger guide, toward the palm heal indicia, may vary to accommodate different sizes of hands, such as an adult male hand versus a child's hand.

Accordingly, an improved hand sizing tool is disclosed. Advantages of the improvements will appear from the drawings and the description of the preferred embodiment.

BRIEF DESCRIPTION OF THE DRAWINGS

In the drawings, wherein like reference numerals refer to similar components.

DETAILED DESCRIPTION OF THE PREFERRED EMBODIMENTS

Figure 1:
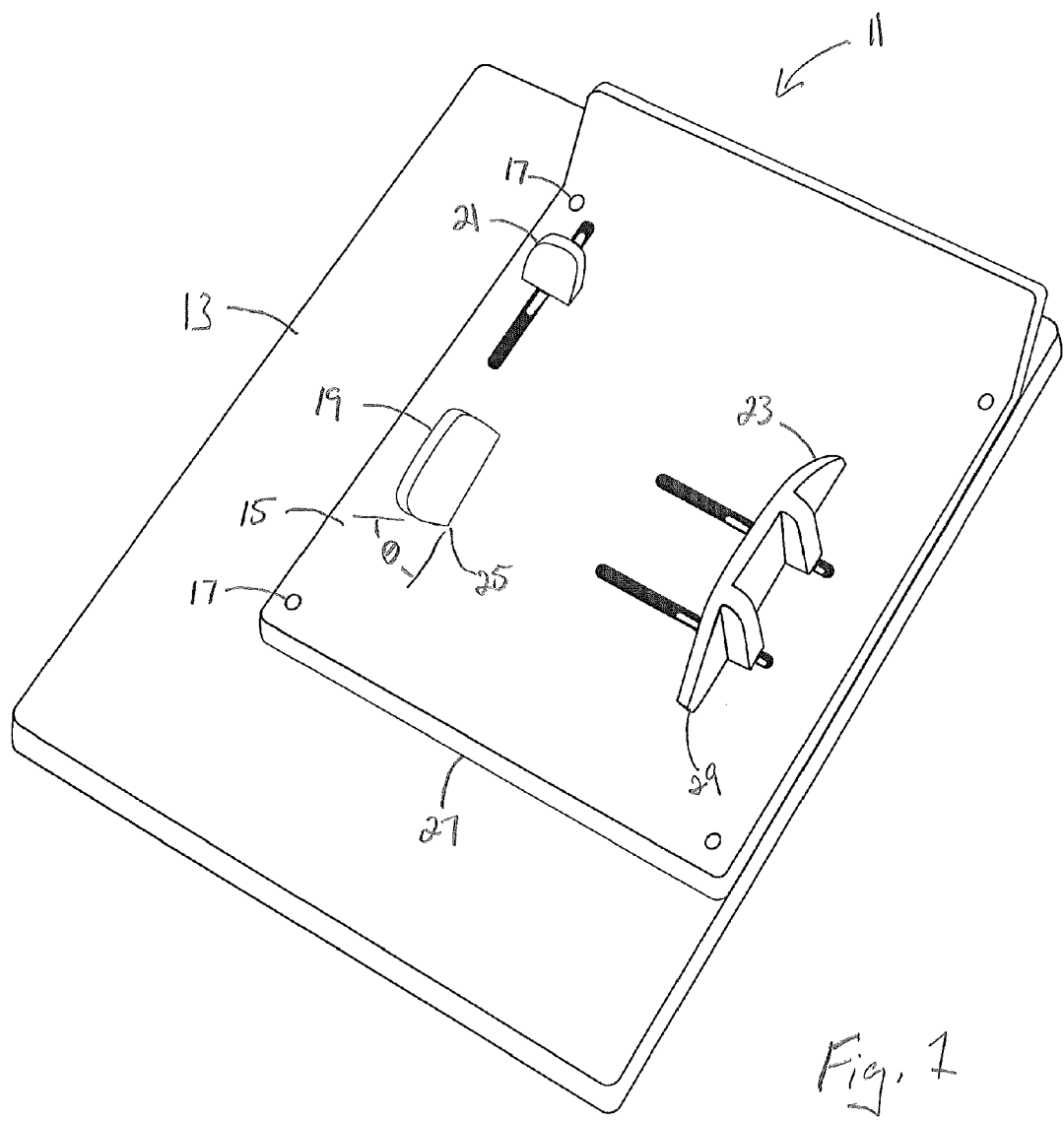
FIG. 1 illustrates a perspective view of a hand sizing tool.

Turning in detail to the drawings, FIG. 1 illustrates a hand sizing tool 11 which may be used to fit gloves to a wearer and facilitate reproducibility of the hand measurements. A base platform 13 has a smaller, secondary platform 15 affixed thereto. These two platforms may be affixed together by any fastener or fastening agent (e.g., glues, epoxies, etc.) according to design preference. As shown, holes 17 for screws (not shown) are included for fastening the platforms 13, 15 together. The base platform 13 serves as a rest for the heel of the palm, and the secondary platform 15 serves as a rest for the upper palm area and the fingers. The other salient features of the hand sizing tool 11 are the index finger guide 19, the index finger measurement slider 21, and the palm width measurement slider 23, each of which extend up and out of the secondary platform 15.

The index finger guide 19, along with the indicia discussed in more detail below, aids in correct placement of a hand on the sizing tool 11. The index finger guide 19 is elongated with a narrow width to fit comfortably between the index finger and the middle finger. The leading edge 25 of the index finger guide 19 forms an angle, θ, of less than 90° with respect to the secondary platform. This angle is preferably set to about 75°, but the angle may be anywhere within the range of about 85° to 60°. This angled leading edge 25 accommodates the anatomical shape of the finger crotch between the index finger and the middle finger when the fingers are held out straight and parallel. This angle also reflects how the finger crotch of gloves are constructed, thereby simulating a glove fit for the hand being measured. When a hand is measured, if the hand is placed snugly against the leading edge 25 of the index finger guide 19, then the gloves fitted will likewise have a snug fit, including at the tip of the index finger. Similarly, if a hand is placed loosely against the leading edge 25 of the index finger guide 19, then the gloves fitted will have a looser fit.

The raised secondary platform 15 aids in measuring the hand in a more relaxed position, which provides for a more user friendly experience and more accurate measurements for fitting a glove to the measured hand. The secondary platform 15 is preferably raised by about 6 mm above the base platform 13, but it may be raised anywhere within the range of about 3 mm to 10 mm.

The leading edge 27 of the secondary platform 15 is positioned to enable the to hand sizing tool 11 to accurately and reproducibly measure hands ranging above the $5^{th}$ percentile of female hand size and below the $95^{th}$ percentile of male hand size. If the leading edge 27 extends too far toward the palm heel, then the relaxing effect realized by having the secondary platform 15 raised may be negated. Similarly, if the leading edge 27 of the secondary platform 15 is too close to the leading edge 25 of the index finger guide 19 (measured from where the leading edge 25 emerges from the secondary platform 27), then the hand being measured is not likely to be sufficiently relaxed to obtain an appropriate measurement for a well-fitting glove. The leading edge 27 of the secondary platform 15 therefore preferably extends beyond the leading edge 25 of the index finger guide 19, toward the heel rest portion of the base platform, by about 23 mm, but it may extend anywhere between about 15 mm to 30 mm.

The palm width measurement slider 23 aids in avoiding confusion about where on the palm the measurement should be taken. In the prior art, such as in U.S. patent publication No. 2003/0056384, the width of the palm might be measured by referencing a line drawn on a paper or other surface, leaving the user to guess at which part of the hand to use for the measurement, since several lines would tend to intersect with the palm. Alternatively, prior art measuring tools simply measure using the widest part of the palm, such as is the case in U.S. Pat. No. 4,173,074. Instead of either of these two approaches, the palm width measurement slider 23 measures from a more specific point on the palm, one which is anticipated to better reflect the width of the hand for purposes of providing a well-fitting glove. In addition, by taking the palm width measurement from this specific point on the hand, the palm width measurement is anticipated to better correlate, especially when combined with the measured index finger length, with other dimensions of the hand, such as finger circumferences, hand circumference, hand length, and finger lengths (of those fingers not directly measured), The measurement end 29 of the palm width measurement slider 23 preferably extends beyond the leading edge 25 of the index finger guide 19, toward the heel rest portion of the base platform, by about 23 mm, but it may extend anywhere between about 15 mm to 30 mm. Here again, the position from which the palm width is measured is intended to enable the to hand sizing tool 11 to accurately and reproducibly measure hands ranging above the $5^{th}$ percentile of female hand size and below the $95^{th}$ percentile of male hand size.

Figure 2:
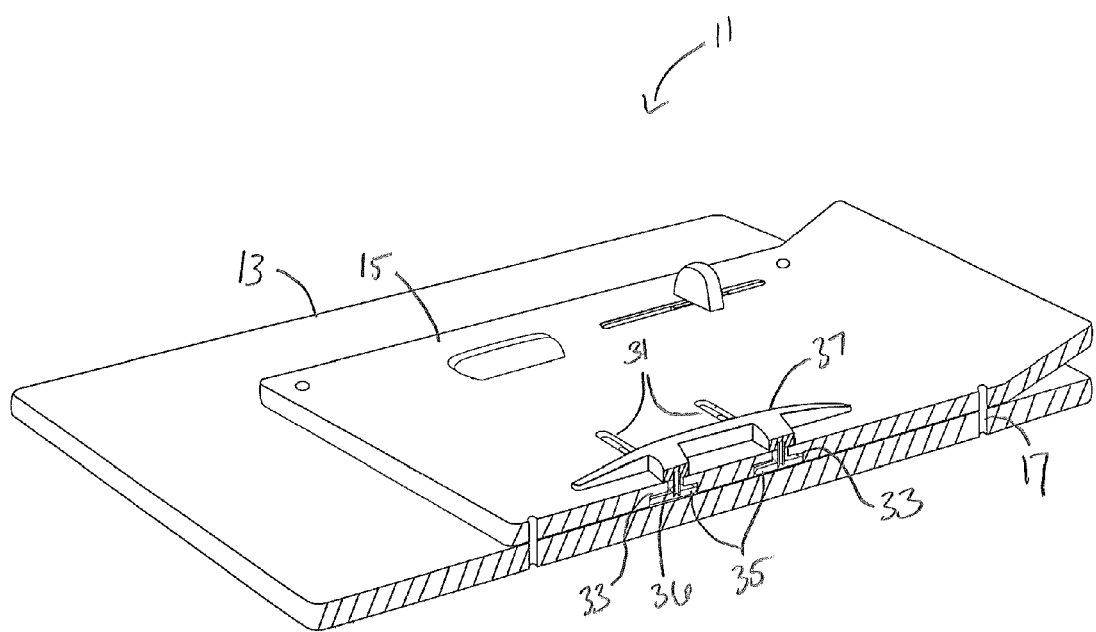
FIG. 2 illustrates a perspective sectional view of a hand sizing tool.

The construction of the measurement sliders 21, 23 is shown in FIG. 2, using the palm width measurement slider 23 as the exemplar. The sliding mechanism for the index finger measurement slider 21 is constructed in essentially the same manner. Slots 31 are formed in the topside of the secondary platform 15, and each slot 31 opens up into a wider groove 33 formed on the underside of the secondary platform 15. Sliding plates 35 are disposed within the grooves 33 and connect through the slots 31 to the slider handle 37 using appropriate fasteners, such as screws 36. The Sliding plates 35 are secured to the slider handle 37 snugly, but without compressing the portions of the secondary platform 15 disposed therebetween, thereby allowing the palm width measurement slider 23 to slide smoothly across the surface of the secondary platform.

Figure 3:
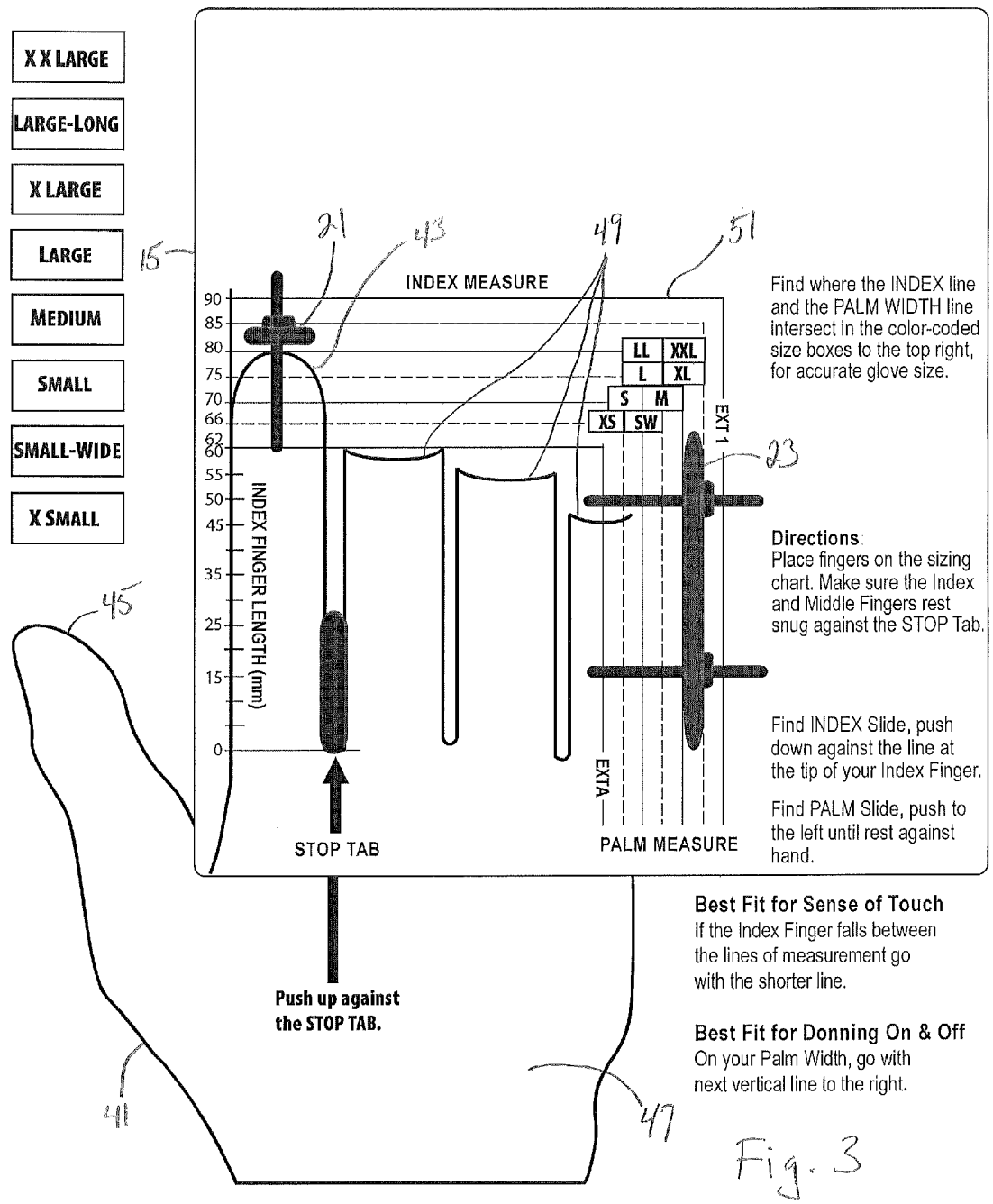
FIG. 3 illustrates a top elevation view of a hand sizing tool, including indicia and instructions.

FIG. 3 illustrates indicia which may be added to the hand sizing tool 11 to aid in its use for accurately measuring a hand. A partial hand 41 is illustrated showing where the hand should be placed on the sizing tool 11 with respect to the secondary platform 15. The partial hand 41 includes the full index finger 43, the thumb 45, the palm 47, and partial fingers 49 for the middle, ring, and little fingers. As shown, the partial hand 41 is a right hand, but hand sizing tools may be constructed for measuring a left hand. As is known in the art of glove sizing, the dominant hand should be measured for fitting a glove. In addition, the indicia provide clear and concise instructions for using the hand sizing tool 11, and guidelines 51 for using the index finger measurement slider 21 and the palm width measurement slider 23 to identify an appropriately sized glove. Although the glove sizes are shown ranging from XS to XXL, they may also be shown in millimeters, which are listed adjacent to the index finger indicia 43, combined with an appropriate descriptor for the width measurement.

Thus, a hand sizing tool is disclosed. While embodiments of this invention have been shown and described, it will be apparent to those skilled in the art that many more modifications are possible without departing from the inventive concepts herein. The invention, therefore, is not to be restricted except in the spirit of the following claims.

What is claimed is:

1. A hand sizing tool comprising:
   a base platform;
   a secondary platform affixed to and raised above the base platform, wherein the platforms include a palm heel indicia on the base platform and an index finger tip indicia on the secondary platform; and
   each of an index finger guide, an index finger measurement slider, and a palm width measurement slider extending out of the secondary platform.

2. The hand sizing tool of claim 1, wherein index finger guide is disposed between the index finger tip indicia and a partial middle finger indicia on the secondary platform.

3. The hand sizing tool of claim 1, wherein a leading edge of the index finger guide extends out of the secondary platform at an angle of less than 90° toward the palm heel indicia.

4. The hand sizing tool of claim 3, wherein the angle is between about 85° and 60°.

5. The hand sizing tool of claim 4, wherein the angle is about 75°.

6. The hand sizing tool of claim 1, wherein the secondary platform is raised above the base platform by between about 3 mm and 10 mm.

7. The hand sizing tool of claim 1, wherein the secondary platform is raised above the base platform by about 6 mm.

8. The hand sizing tool of claim 1, wherein a measurement end of the palm width measurement slider extends beyond a leading edge of the index finger guide, toward the palm heel indicia, by between about 10 mm and 22 mm.

9. The hand sizing tool of claim 1, wherein a measurement end of the palm width measurement slider extends beyond a leading edge of the index finger guide, toward the palm heel indicia, by about 15 mm.

10. The hand sizing tool of claim 1, wherein an edge of the secondary platform extends beyond a leading edge of the index finger guide, toward the palm heel indicia, by between about 15 mm to 30 mm.

11. The hand sizing tool of claim 1, wherein an edge of the secondary platform extends beyond a leading edge of the index finger guide, toward the palm heel indicia, by about 23 mm.

* * * * *